US00PP18984P2

(12) United States Plant Patent
Hanes

(10) Patent No.: US PP18,984 P2
(45) Date of Patent: Jun. 24, 2008

(54) ***VERBENA* PLANT NAMED 'RAP LILLA'**

(50) Latin Name: *Verbena hybrida×tenuisecta*
Varietal Denomination: Rap Lilla

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/709,472

(22) Filed: Feb. 22, 2007

(51) Int. Cl.
*A01H 5/00* (2006.01)

(52) U.S. Cl. ..... Plt./308
(58) Field of Classification Search ..... Plt./308
See application file for complete search history.

*Primary Examiner*—Kent L Bell
(74) *Attorney, Agent, or Firm*—Jondle & Associates, P.C.

(57) ABSTRACT

A *verbena* cultivar particularly distinguished by purple-violet colored flowers, vigorous and free-branching with multiple secondary lateral branches, low, outwardly spreading, compact growth habit, and tolerance to powdery mildew is disclosed.

2 Drawing Sheets

Genus and species: *Verbena hybrida×tenuisecta.*
Variety denomination: 'Rap Lilla'.

BACKGROUND OF THE NEW PLANT

The present invention comprises a new and distinct cultivar of *verbena,* botanically known as *Verbena hybrida× tenuisecta,* and hereinafter referred to by the cultivar name 'Rap Lilla'. The new cultivar originated in 2004 in Gilroy, Calif. from an hybridization between the female *verbena* parent 'Rap Viotwo' (U.S. Plant Pat. No. 18,384), with a deep violet-blue flower color and the male *verbena* parent, '1668-1', an unpatented proprietary line with a deep purple-blue flower color.

The seeds produced by pollination were sown in June 2004. A single plant selection was chosen for further evaluation and for asexual propagation in September 2004.

The new cultivar was created in 2004 in Gilroy, Calif. and has been asexually reproduced repeatedly by vegetative cuttings and tissue culture in Gilroy, Calif. and Andijk, The Netherlands over a two-year period. The plant has also been trialed at Gilroy, Calif., Andijk, The Netherlands and Hillscheid, Germany. The present invention has been found to retain its distinctive characteristics through successive asexual propagations.

Plant Breeder's Rights for this cultivar have been applied for in Switzerland on Oct. 30, 2006.

SUMMARY OF THE INVENTION

The following are the most outstanding and distinguishing characteristics of the new cultivar when grown under normal horticultural practices in Gilroy, Calif. and Andijk, The Netherlands.

1. Purple-violet flower color;
2. Low, outwardly spreading, compact growth habit;
3. Vigorous and free branching with multiple secondary lateral branches; and
4. Tolerance to powdery mildew.

DESCRIPTION OF PHOTOGRAPHS

This new *verbena* plant is illustrated by the accompanying photographs which show overall plant habit, including blooms, buds and foliage of the plant. The photographs were taken of 20 to 23 week old plants, grown in a greenhouse in the late spring months, before being moved to an outdoor setting during the summer. The photographs were taken in August 2006. The color shown are as true as can be reasonably obtained by conventional photographic procedures.

Figure 1:
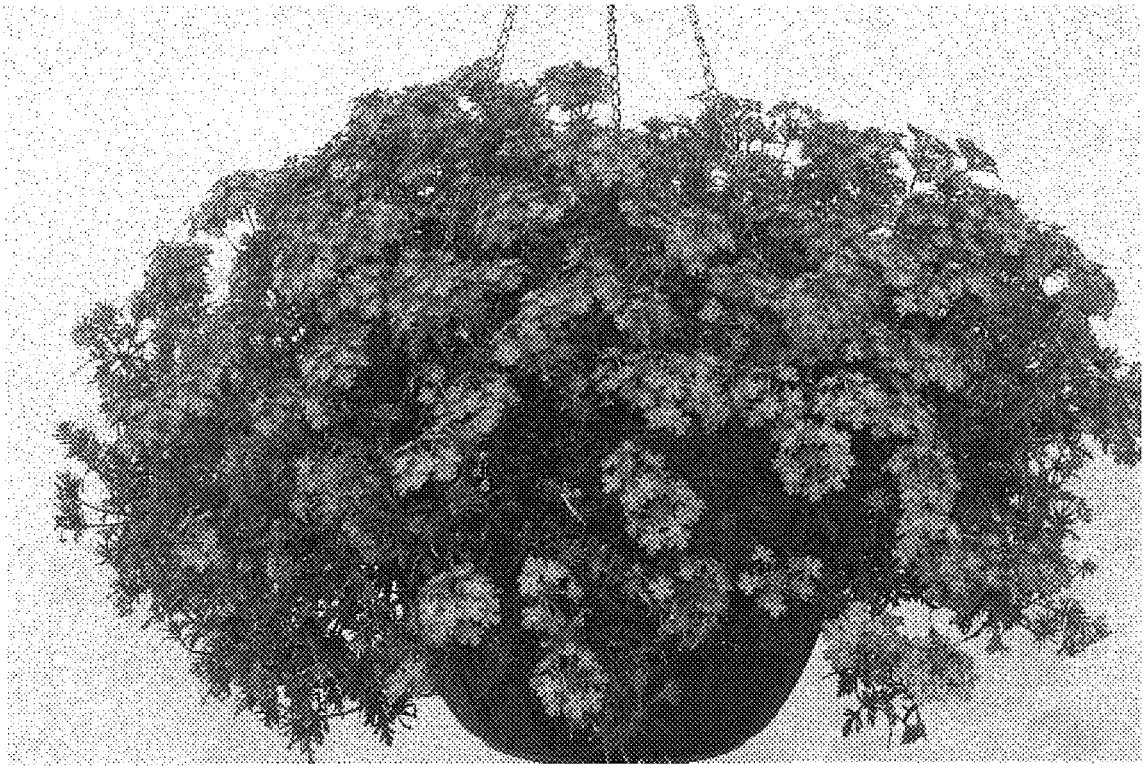

FIG. 1. shows a close up of the inflorescences in a flower box, in Andijk, The Netherlands.

Figure 2:
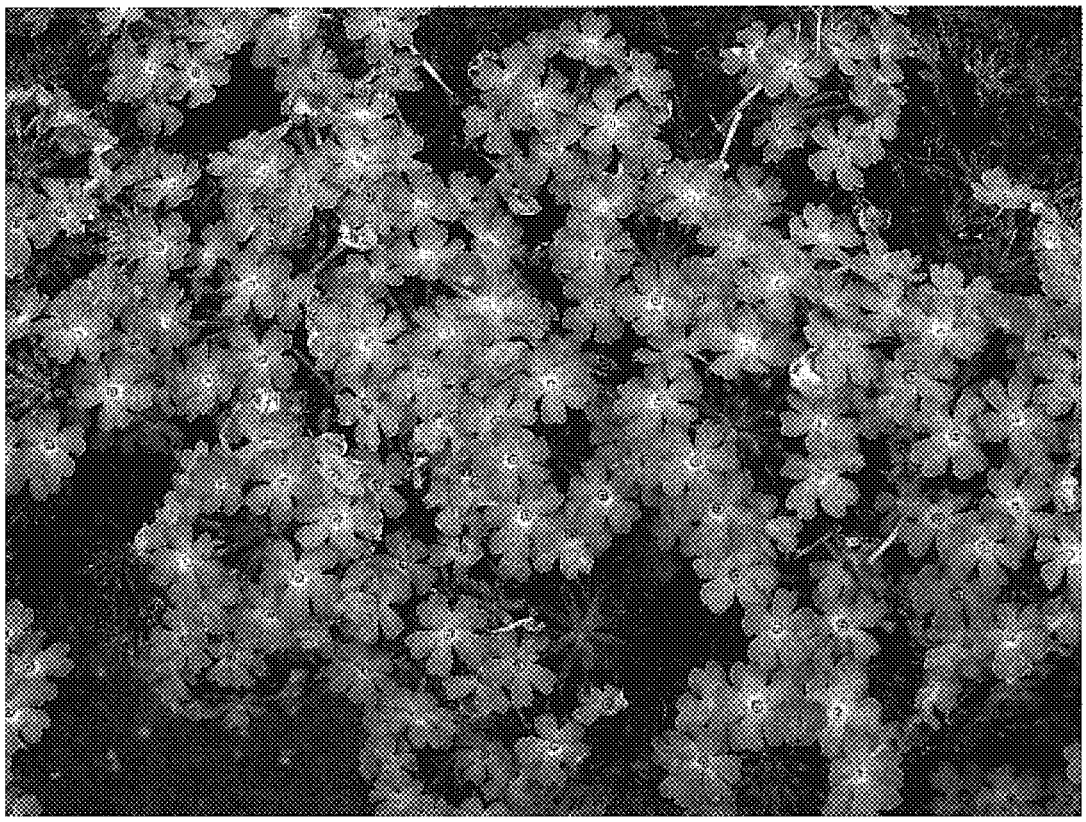

FIG. 2. shows the overall plant habit, including blooms buds and foliage of plants in a hanging basket in Hillscheid, Germany.

DESCRIPTION OF THE NEW CULTIVAR

The following detailed descriptions set forth the distinctive characteristics of 'Rap Lilla'. The data which define these characteristics were collected from asexual reproductions carried out in Gilroy, Calif. The plant history was taken from plants approximately 12-weeks old, grown in 4-inch pots, in Gilroy, Calif. in the fall and winter seasons. The plants had one plant growth regulator treatment and one terminal pinch at the onset of the trial. Color readings were taken in a LEXAN-covered greenhouse in January under natural light. Color references are primarily to the R.H.S. Colour Chart of The Royal Horticultural Society of London (R.H.S.) (2001 edition). Texture description details were observed with a dissecting microscope.

DETAILED BOTANICAL DESCRIPTION

Classification:
*Botanical.—Verbena hybrida×tenuisecta.*
*Common name.—Verbena.*

Parentage:
*Female.*—'Rap Viotwo' (U.S. Plant Pat. No. 18,384), having a deep violet-blue flower color.
*Male.*—'1668-1' (unpatented) proprietary line having a deep purple-blue flower color.

Growth:

*Form.*—Herbaceous annual; low, outwardly spreading, compact, with a decumbent plant habit.

*Growth and branching habit.*—Vigorous and free-branching with multiple secondary lateral branches.

*Height* (*measured from the top of the soil, including flowers*).—5.0 cm to 6.0 cm.

*Width* (*horizontal plant diameter*).—40.0 cm to 45.0 cm.

*Time to produce a finished flowering plant.*—Approximately 10 weeks for a 12-cm pot in the spring.

*Outdoor plant performance.*—Use in containers, hanging baskets and garden beds.

*Time to initiate and develop roots.*—Approximately 7 to 10 days at 22 to 24 degrees Celsius.

*Root description.*—Fibrous, fleshy, white.

Leaves:

*Arrangement.*—Opposite.

*Immature leaf.*—Color: Upper surface: RHS 137A, glossy. Lower surface: RHS 137C.

*Mature leaf.*—Color: Upper surface: Closest to RHS 137A. Lower surface: RHS 137D. Length: 2.9 cm to 3.4 cm. Width: 2.7 cm to 3.5 cm. Shape: Ovate; pinnatisect. Apex: Acute. Base: Attenuate. Margin: Dentate, incised. Texture: Upper surface: Hirsute. Lower surface: Hirsute only on the veins. Venation: Pinnate. Venation color: RHS 144A.

*Petioles.*—Length: 0.4 cm to 0.5 cm. Diameter: 0.15 cm to 0.2 cm. Color: Between RHS 144A and RHS 144B. Texture: Hirsute.

Stems:

*Number of branches per plant.*—5 to 8 main branches.

*Color.*—RHS 146B.

*Length.*—25.0 cm to 30.0 cm.

*Diameter* (*measured from the midpoint*).—0.2 cm to 0.3 cm.

*Internode length.*—1.7 cm to 2.5 cm.

*Texture.*—Pilose; hirsute; some glandular hairs.

*Stem anthocyanin.*—Absent.

Flower buds:

*Color* (*at tight bud*).—RHS 86B.

*Shape.*—Tubular.

*Diameter.*—0.25 cm.

*Length.*—1.7 cm to 1.9 cm.

Inflorescence:

*Blooming habit.*—Flowers continuously from spring through fall; flowers appear about 9 to 10 weeks after planting of rooted cuttings.

*Lastingness of individual blooms on the plant.*—5 to 7 days.

*Fragrance.*—Absent.

*Inflorescence type.*—Terminal spike.

*Horizontal diameter of inflorescence.*—4.6 cm to 5.2 cm.

*Vertical diameter of inflorescence.*—3.0 cm to 3.5 cm.

*Number of florets per raceme.*—45 to 53.

*Peduncle.*—Color: RHS 146B. Diameter: 0.2 cm. Length: 2.3 cm to 3.0 cm. Texture: Hirsute; pillose; glandular hairs, most with a violet color.

Flowers:

*Floret form.*—Salverform; flowers sessile, not persistent.

*Diameter.*—1.3 cm to 1.4 cm.

*Number of petals and arrangement.*—Each floret is composed of 5 petals fused at the base.

*Immature flower.*—Color: Upper surface: A little lighter than RHS N82A. Lower surface: Closest to RHS N82C, a little lighter towards the corolla tube; and RHS N155D around corolla tube.

*Mature flower.*—Color: Upper surface: Closest to RHS N82A. Lower surface: Closest to RHS N82C. Corolla: Tube color (inside): RHS N155D. Tube color (outside): RHS N155D, with shades of RHS N82B. Tube length: 1.9 cm to 2.3 cm.

*Petals.*—Size: Length: 0.7 cm to 0.8 cm. Width: 0.6 cm to 0.7 cm. Lobe shape: Obovate. Apex: Emarginate. Base: Fused. Margin: Entire. Texture: Papillose.

*Calyx.*—Sepals: Five sepals whose margins are fused to each other along their length, with a transparent membrane of less than 0.1 cm in width and with one smaller sepal (0.6 cm) attached to the base of the calyx. General color: RHS 143A for the outer surface; inner surface was not observed. Length: 1.1 cm to 1.2 cm. Width: 0.3 cm. Shape: Linear. Apex: Acute. Base: Fused. Margin: Fused. Texture: Pilose, some glandular hairs, all with a violet color.

Reproductive organs:

*Stamens.*—Anthers and filaments are fused to the upper half of the corolla tube.

*Anther quantity.*—Four with two pollen sacs per anther.

*Anther length.*—0.1 cm.

*Pollen.*—Amount: Scant to moderate. Color: A little lighter than RHS 1B.

*Pistil.*—1.

*Style length.*—1.6 cm to 1.7 cm.

*Style color.*—*RHS* 145C.

*Stigma color.*—RHS 146D.

Fruit/Seed set: Have not been produced.

Disease and Insect resistance: Tolerant to powdery mildew

COMPARISON WITH PARENTAL AND COMMERCIAL CULTIVARS

'Rap Lilla' differs from the female parent, 'Rap Viotwo' (U.S. Plant Pat. No. 18,384) in that 'Rap Lilla' has a lighter flower color, a more compact habit and smaller leaves than 'Rap Viotwo'. 'Rap Viotwo' has larger, darker and less incised foliage than 'Rap Lilla'. Additionally, 'Rap Viotwo' has deeper depth to the inflorescence and less branching than 'Rap Lilla'.

'Rap Lilla' differs from the male proprietary parent, '1668-1' (unpatented) in that '1668-1' has a deeper purple-blue color than 'Rap Lilla' '1668-1' has larger, darker and less incised foliage than 'Rap Lilla'. Additionally, '1668-1' has deeper depth to the inflorescence and less branching than 'Rap Lilla'.

I claim:

1. A new and distinct cultivar of *verbena* plant as shown and described herein.

* * * * *